(12) United States Patent
Ketelson et al.

(10) Patent No.: US 8,257,745 B2
(45) Date of Patent: Sep. 4, 2012

(54) USE OF SYNTHETIC INORGANIC NANOPARTICLES AS CARRIERS FOR OPHTHALMIC AND OTIC DRUGS

(75) Inventors: Howard Allen Ketelson, Dallas, TX (US); David L. Meadows, Colleyville, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/186,108

(22) Filed: Jul. 19, 2011

(65) Prior Publication Data

US 2011/0274760 A1   Nov. 10, 2011

Related U.S. Application Data

(63) Continuation of application No. 10/494,709, filed as application No. PCT/US02/41248 on Dec. 20, 2002.

(60) Provisional application No. 60/342,983, filed on Dec. 21, 2001.

(51) Int. Cl.
| | |
|---|---|
| *A61K 9/14* | (2006.01) |
| *A61K 38/18* | (2006.01) |
| *A61P 27/06* | (2006.01) |
| *A61P 25/00* | (2006.01) |
| *A61P 31/00* | (2006.01) |
| *A61P 29/00* | (2006.01) |
| *A61P 37/08* | (2006.01) |
| *A61P 37/02* | (2006.01) |
| *B82Y 5/00* | (2011.01) |

(52) U.S. Cl. .......... 424/489; 514/9.6; 977/775; 977/906

(58) Field of Classification Search ................... 424/489; 514/9.6; 977/775, 906

See application file for complete search history.

(56) References Cited

U.S. PATENT DOCUMENTS

| | | | |
|---|---|---|---|
| 3,884,826 A | 5/1975 | Phares et al. | |
| 3,947,573 A | 3/1976 | Rankin | |
| 4,120,949 A | 10/1978 | Bapatia et al. | |
| 4,127,423 A | 11/1978 | Rankin | |
| 4,271,143 A | 6/1981 | Schoenwald et al. | |
| 4,365,030 A | 12/1982 | Oswald et al. | |
| 4,374,745 A | 2/1983 | Sibley et al. | |
| 4,394,179 A | 7/1983 | Ellis et al. | |
| 4,804,539 A | 2/1989 | Guo et al. | |
| 4,847,078 A | 7/1989 | Sheppard et al. | |
| 4,891,043 A | 1/1990 | Zeimer et al. | |
| 4,923,699 A | 5/1990 | Kaufman | |
| 4,940,701 A | 7/1990 | Davis et al. | |
| 5,037,647 A | 8/1991 | Chowhan et al. | |
| 5,106,615 A | 4/1992 | Dikstein | |
| 5,139,782 A | 8/1992 | Jung | |
| 5,185,152 A | 2/1993 | Peyman | |
| 5,212,162 A | 5/1993 | Missel et al. | |
| 5,403,598 A | 4/1995 | Beck et al. | |
| 5,585,108 A | 12/1996 | Ruddy et al. | |
| 5,654,262 A | 8/1997 | Desai et al. | |
| 5,674,504 A | 10/1997 | Kaufmannn | |
| 5,741,817 A | 4/1998 | Chowhan et al. | |
| 5,811,580 A | 9/1998 | Rhubright | |
| 5,858,346 A | 1/1999 | Vehige et al. | |
| 6,015,816 A | 1/2000 | Kostyniak et al. | |
| 6,024,941 A | 2/2000 | Yanagida et al. | |
| 6,143,799 A | 11/2000 | Chowhan et al. | |
| 6,177,480 B1 | 1/2001 | Tsuzuki et al. | |
| 6,180,093 B1 | 1/2001 | De et al. | |
| 6,271,224 B1 | 8/2001 | Kapin et al. | |
| 6,309,658 B1 | 10/2001 | Xia et al. | |
| 6,319,464 B1 | 11/2001 | Asgharian | |
| 6,319,513 B1 | 11/2001 | Debrozsi et al. | |
| 6,333,054 B1 * | 12/2001 | Rogozinski | ................... 424/661 |
| 6,403,609 B1 | 6/2002 | Asgharian | |
| 2002/0035264 A1 | 3/2002 | Kararli et al. | |
| 2004/0076682 A1 | 4/2004 | Kohzaki et al. | |

FOREIGN PATENT DOCUMENTS

| | | |
|---|---|---|
| EP | 0217440 | 4/1987 |
| EP | 1008340 A2 | 6/2000 |
| EP | 0947203 B1 | 2/2003 |
| EP | 1366758 | 12/2003 |
| JP | 9285529 | 11/1997 |
| JP | 2001240547 | 9/2001 |
| WO | WO8805073 A1 | 7/1988 |
| WO | WO9731709 A1 | 9/1997 |
| WO | WO9932158 A3 | 7/1999 |
| WO | WO0010527 | 3/2000 |
| WO | WO0046147 A2 | 8/2000 |
| WO | WO02064114 | 8/2002 |
| WO | WO03011351 A2 | 2/2003 |
| WO | 03059194 | 7/2003 |
| WO | 03059263 | 7/2003 |

OTHER PUBLICATIONS

Voet and Voet. Biochemistry 2E, pp. 37-38 (1995).*
Merck Veterinary Manual, 9E: Ophthalmic Drugs—Routes of Administration (2005).*
Kreuter, J., Nanoparticles, Colloidal Drug Delivery Systems, 1994, pp. 219-342, Chapter 5, edited by Jork Kreuter, Marcel Dekker, New York (USA).
Grandolini, et al, Intercalculation Compounds of Hydrotalcite-like Anionic Clays With Anti-inflammatory Agents—I. Intercalculation and in vitro Release of Ibuprofen, International Journal of Pharmaceutics, 2001, pp. 23-32, vol. 220.
Plaizier-Vercammen, Rheological Properties of Laponite XLG, A Synthetic Purified Hectorite, Pharmazie, 1992, pp. 856-861, vol. 47.

(Continued)

*Primary Examiner* — Barbara P Badio
*Assistant Examiner* — Sara E Townsley
(74) *Attorney, Agent, or Firm* — Gregg C. Brown; Michael D. Rein

(57) ABSTRACT

The use of nanoparticles of inorganic materials (e.g., synthetic smectite clays) in ophthalmic and otic pharmaceutical compositions is described. The nanoparticles are utilized as biologically inert carriers or depots for ophthalmic and otic drugs. The nanoparticles may also be utilized to modify the rheological properties of the compositions, so as to enhance the viscosity or flow characteristics of the compositions and/or increase the retention time of the compositions in the eye or ear.

19 Claims, No Drawings

OTHER PUBLICATIONS

Biosante, BioSante Pharmaceuticals Announces Positive Insullin Pre-Clinical Trial Results, www.biosantepharma.com, Nov. 5, 2001, p. 1.

Biosante, CAP Calcium Phosphate Nanoparticles a Novel Vaccine Adjuvant and Delivery System, www.biosantepharma.com, p. 1, (2001).

Biosante, BioSante Pharmaceuticals, Inc. Announces Positive Pre-Clinical IntraOcular Trial Results, www.biospace.com, Jan. 7, 2002, pp. 1-3.

Tiffany, Viscoelastc Properties of Human Tears and Polymer Solutions; Lacrimal Gland, Tear Film and Dry Eye Syndromes, 1994, pp. 267-270, Plenum Press, NY.

Calvo, Comparative in vitro Evaluation of Several Collodial Systems, Nanoparticles, Nanocapsules, and Nanoemulsions, as Ocular Drug Carriers, Journal of Pharmaceutical Sciences, 1996, pp. 530-536, vol. 85, No. 5.

Zimmer, Microspheres and Nanoparticles Used in Ocular Delivery Systems, Advanced Drug Delivery Reviews, 1995, pp. 61-73, vol. 16.

Gieseking, The Mechanism of Cation Exchange in the Montmorilonite-Beidellite-Nontronite Type of Clay Materials, Soil Science, 1939, pp. 1-14, vol. 47.

Contact Lenses Used to Deliver Eye Drugs, R&D Digest, Medical Devicelink, www.devicelind.com, May 2003, pp. 1-2.

Gulsen, et al., A Novel Ophthalmic Drug Delivery Vehicle: Dispersion of Nanoparticles in Soft Contact Lenses, American Chemical Society Symposium, 225th ACS National Meeting, New Orleans, Mar. 2003, p. 1.

Clay Delivers DNA for Gene Therapy, C&EN, Nov. 20, 2000, p. 41.

Fielder Lexikon der Hilsstoffe, Ed.: Hoepfner, E.-M., Reng, A., and Schmidt Fifth Edition, Editio Cantor Verlag Auelndorf, Germany, p. 354, 5th Edition (2002).

Handbook of Pharamceutical Excipients, American Pharmaceutical Association, Washington, DC, US, and the Pharmaceutical Society of Great Britain, London, England, 1988, excerpt pp. 253-256.

Lehrbuch der Pharmazeutischen Technologie, Bauer, KH, Fromming, K.H.; and Fuhrer, C., 1999, Wissenschaftliche Verlagsgescellschaft mbH Stuttgart, excerpt pp. 229-230.

Contact Lenses that Dispense Prescription Drugs, American Chemical Society, Public Release, Mar. 23, 2002, p. 1.

* cited by examiner

USE OF SYNTHETIC INORGANIC NANOPARTICLES AS CARRIERS FOR OPHTHALMIC AND OTIC DRUGS

This application is a continuation of U.S. application Ser. No. 10/494,709 filed May 6, 2004, now pending, which is a National Stage Entry of International Patent Application No. PCT/US02/41248 filed Dec. 20, 2002, which claims the benefit of U.S. Provisional Application No. 60/342,983 filed Dec. 21, 2001, the entire contents of which are hereby incorporated herein by reference.

BACKGROUND OF THE INVENTION

The present invention is directed to the field of ophthalmic and otic drug delivery. More specifically, the present invention is directed to the use of synthetic, inorganic nanoparticles as inert carriers for ophthalmic and otic drugs, and to the use of pharmaceutical compositions based on the invention to deliver ophthalmic drugs topically to the eye and ear.

Many different types of agents have been utilized as carriers for delivering ophthalmic drugs to the eye. For example, the use of carboxyvinyl polymers for this purpose is described in U.S. Pat. No. 4,271,143. Various other organic polymers have also been utilized as carriers for ophthalmic drugs.

The use of nanoparticles formed from synthetic or natural polymers in ophthalmic compositions has been described in various scientific publications, such as:

Kreuter, J. "Nanoparticles" *Colloidal Drug Delivery Systems*, edited by Jork Kreuter, Marcel Dekker, New York, N.Y. (USA), chapter 5, page 219 (1994);

Gurny, R. "Ocular therapy with nanoparticles" *Polymeric Nanoparticles and Microspheres* edited by P. Guiot and P. Couvreur, Boca Raton, Fla. (USA): CRC Press, page 127 (1986);

Gurny, R. "Preliminary study of prolonged acting drug delivery system for the treatment of glaucoma" *Pharm Acta Helv.*, volume 56, page 130 (1981);

Zimmer, et al. "J. Microspheres and nanoparticles used in ocular delivery systems" *Advanced Drug Delivery Reviews*, volume 16, number 1, pages 61-73 (1995); and Calvo, et al. "Comparative in vitro evaluation of several colloidal systems, nanoparticles, nanocapsules, and nanoemulsions, as ocular drug carriers" *J Pharm Sci*, volume 85, number 5. pages 530-536 (May 1996).

The nanoparticles utilized in the present invention are not formed from synthetic or natural polymers such as those described in the above-cited publications. Rather, the present invention is directed to the use of inorganic nanoparticles. The nanoparticles utilized in the present invention include, for example, clay substances that are water swellable. An extensive review of clays and their chemical and physical properties can be found in:

Giese, R. F. and van Oss C. J., "Colloid and Surface Properties of Clays and Related Minerals", A. T. Hubbard, Marcel Dekker Inc., Vol. 105.

The preferred nanoparticles are formed from synthetic smectite clays which are prepared from simple silicates. The following publications may be referred to for further background regarding the use of synthetic clay nanoparticles in pharmaceutical compositions:

Plaizier-Vercammen, "Rheological properties of Laponite XLG, a synthetic purified hectorite" *Pharmazie*, volume 47, page 856 (1992);

Grandolini, et al. "Intercalation compounds of hydrotalcite-like anionic clays with anti-inflammatory agents: I. Intercalation and in vitro release of ibuprofen" *International Journal of Pharmaceutics*, volume 220, numbers 1-2, pages 23-32 (Jun. 4, 2001);

U.S. Pat. No. 5,585,108 (Ruddy, et al.) entitled "Formulations of Oral Gastrointestinal Therapeutic Agents in Combination with Pharmaceutically Acceptable Clays";

U.S. Pat. No. 6,177,480 B1 (Tsuzuki, et al.), which describes the use of a synthetic clay material (i.e., Laponite™) as a wetting agent for contact lenses and to assist in the removal of lipid deposits from contact lenses by surfactants;

U.S. Pat. No. 6,015,816 (Kostyniak, et al.), which describes an improved method using colloid particles, such as smectite clay minerals, as a substrate for ligands having antimicrobial activity, so as to control microbial growth on a material; and U.S. Pat. No. 6,177,480 (Tsuzuki, et al.) describes the use of synthetic clay material (i.e., Laponite™) as a wetting agent for contact lenses and to assist in the removal of lipid deposits from contact lenses by surfactants.

SUMMARY OF THE INVENTION

The present invention is based on the use of nanoparticles of inorganic materials to facilitate the formulation of ophthalmic and otic compositions, particularly compositions adapted for topical application to ophthalmic or otic tissues. The nanoparticles function as a chemically inert carrier or depot for ophthalmic and otic drugs and other components of ophthalmic and otic compositions.

The present invention is believed to have advantages over the prior art use of organic polymers for ophthalmic drug delivery. For example, the inorganic nanoparticles utilized in the present invention are particularly well suited for use as drug delivery agents in instances wherein controlled delivery of the drug is needed. The particles offer advantages over current state of the art delivery agents as a result of the higher surface area of the particles and the ability of the particles to form clear gels or solutions when dispersed in aqueous media.

It has been found that at very low concentrations in aqueous solutions, the nanoparticles can be dispersed while retaining a clear solution. Due to the minute size of the nanoparticles, the compositions of the present invention remain clear and non-blurry, which is very important for ophthalmic compositions. It has also been found that the particles can be utilized as carriers for ophthalmic and otic drugs without compromising the microbiological activity of antimicrobial preservatives contained in the compositions.

In addition to acting as inert carriers for ophthalmic and otic drugs, the inorganic nanoparticles also provide advantageous rheological properties for the compositions of the present invention.

DETAILED DESCRIPTION OF THE INVENTION

The nanoparticles utilized in the present invention are inorganic materials. The particles have colloidal dimensions, a large surface area and a high ion exchange capacity. The particles are generally referred to hereinafter as "inorganic nanoparticles". The use of the synthetic inorganic nanoparticles is preferred.

The inorganic nanoparticles used in the present invention preferably have particle dimensions less than 100 nanometers ("nm"), but greater than 1 nm. The morphology of the nanoparticles is not limited to being spherical; plate-like, cubic, ellipsoid or other particle shapes are also useful. The particles have surface areas ranging from 30-1000 square meters/gram ("m$^2$/g"), and have an overall negative surface charge at a pH in the range of 6.0 to 7.8.

The inorganic nanoparticles utilized in the present invention may also be surface modified, depending on the particular type of composition involved and stability requirements. Different types of nanoparticles may be combined to optimize the formulation properties.

The inorganic nanoparticles utilized in the present invention are preferably formed from clays that swell in aqueous solutions. These types of clays are referred to herein as being "hydrous". The use of nanoparticles of synthetic hydrous clays is preferred due to the commercial availability, purity, and well-defined chemical composition and physical properties of these materials. In addition, the synthetic clay nanoparticles are easier to formulate and can form colorless and transparent gels more readily than inorganic nanoparticles formed from naturally occurring clays.

Synthetic inorganic nanoparticles that are particularly useful include a synthetic smectite clay that is commercially available under the trademark Laponite® (Southern Clay Products, Gonzales, Tex., USA). Laponite® is a layered hydrous magnesium silicate to prepared from simple silicates. The following publication may be referred to for further details concerning the physical properties and functions of Laponite®: "Laponite Technical Bulletin "Laponite-synthetic layered silicate—its chemistry, structure and relationship to natural clays" L204/01 g. Another synthetic magnesium aluminum silicate material is also commercially available under the trademark OPTIGEL® SH (Sud-Chemie, Louisville, Ky.).

Inorganic nanoparticles formed from naturally occurring hydrous clays may also be utilized, either in combination with a synthetic clay or alone. Examples of suitable naturally occurring clays include aliettite, beidellite, bentonite, hectorite, kaolinite, magadite, montmorillonite, nontronite, saponite, sauconite, stevensite and volkonskoite.

The following publications may be referred to for further details regarding the physical properties of various types of clay nanoparticles and the use of these materials as ion-exchange materials, viscosity modifiers and film forming agents:

Gieseking, J. E., "Mechanism of Cation Exchange in the Mont-Morillonite-Beidellite-Nontronite Type of Clay Minerals", *Soil Science*, volume 47, pages 1-14 (1939);

Theng, B. K. G., "Formation and Properties of Clay-Polymer Complexes", Elsevier, Amsterdam, (1979); and H. van Olphen, "Clay Colloid Chemistry", Krieger Publishing Company, Florida, Second Edition (1991).

Examples of other inorganic nanoparticle materials that may be utilized instead of or in combination with the clay nanoparticles described above include zeolites, silica, aluminum oxide, cerium oxide, titanium oxide and zinc oxide. Nanometer sized silica particles, such as those supplied by Nalco (e.g., Nalco® 115 and 1140) and EKA Chemicals (NYACOL® grades), are readily available. Mineral oxide nanoparticles based on other metals are also commercially available. For example, mineral oxides (e.g., aluminum oxide, cerium oxide, titanium oxide and zinc oxide) having well defined nano-dimensions are available from Nanophase Technologies (Romeoville, Ill., USA) under the trade name "NanoTek®".

As indicated above, it has been discovered that the above-described inorganic nanoparticles are capable of functioning as carriers for ophthalmic and otic drug molecules and other components of ophthalmic and otic pharmaceutical compositions. The present invention is applicable to the use of nanoparticles as carriers for various types of pharmaceutically active agents, such as agents for controlling intraocular pressure and treating glaucoma, neuroprotectants, anti-allergy agents, anti-infectives, anti-inflammatory agents, mucosecretagogues, angiostatic steroids, pain relievers, decongestants or astringents, and so on.

Examples of pharmaceutically active agents which may be included in the compositions of the present invention, and administered via the methods of the present invention include, but are not limited to: anti-glaucoma agents, such as apraclonidine, brimonidine, betaxolol, timolol, pilocarpine, carbonic anhydrase inhibitors, prostaglandins and serotonergics; dopaminergic antagonists; anti-infectives, such as moxifloxacin, gatifloxacin, levofloxacin, ciprofloxacin and tobramycin; non-steroidal and steroidal anti-inflammatories, such as rimexolone, dexamethasone, prednisolone, fluorometholone, lotoprednol, naproxen, diclofenac, suprofen and ketorolac; proteins; growth factors, such as epidermal growth factor; mucosecretagogues, such as 15-HETE; angiostatic steroids, such as anecortave acetate; antihistamines, such as emadine; mast cell stabilizers, such as olopatadine; and immunomodulators, such as cyclosporin.

The concentration of the inorganic nanoparticles utilized in specific ophthalmic or otic compositions of the present invention will depend on the physical form of the composition (e.g., solution, dispersion, suspension or gel) and other factors apparent to those skilled in the art. The identification of an ideal concentration of nanoparticles for a specific formulation can be determined by means of routine experimentation, conducted in accordance with the specifications and considerations described herein. The ideal concentrations selected as a result of such testing may vary significantly from formulation to formulation, but the concentrations will generally fall within the range of 0.1 to 10 w/v %. The concentration of dispersed smectite clay nanoparticles (e.g., Laponite®) in the compositions of the present invention may vary significantly from formulation to formulation, but is normally within the range of 0.1 to 1 w/v %, and preferably within the range of 0.3 to 0.5 w/v %.

It has been found that at low concentrations in aqueous buffered solutions, the above-described inorganic nanoparticles can be dispersed under physiological pH conditions while retaining a transparent solution, dispersion or gel. The inorganic nanoparticles will form clear and colorless dispersions of low viscosity at concentrations of up to 10 w/v %. However, if combined with appropriate amounts of salts and other excipients, the nanoparticles will form clear, highly shear thinning, thixotropic gels. More particularly, at concentrations of greater than 0.5 weight/volume percent ("w/v %"), the particles will form clear gels under appropriate electrolyte conditions and display lubrication, film forming and viscoelastic properties.

The electrolyte conditions required for the formation of such gels will vary somewhat depending on the particular type of inorganic nanoparticle selected, the concentration utilized, the type of buffer or vehicle involved and other factors apparent to persons skilled in the art. However, the preferred electrolyte conditions will generally involve the use of very low levels of 1:1 electrolytes (e.g., NaCl). The ideal concentration of the electrolyte in the gel compositions of the present invention can be readily determined through routine experimentation for each formulation. However, the amount of electrolyte required will generally be on the order of 0.01 to 0.1 w/v %.

The incorporation of inorganic nanoparticles in aqueous ophthalmic and otic compositions as described herein results in significant rheological changes. The compositions of the present invention will typically have viscosities that are orders of magnitude higher than the viscosities of compositions that are identical, except for the inclusion of synthetic inorganic nanoparticles. The compositions of the present invention will preferably have a viscosity of less than 5.0 milliPascal second ("mPa*sec") at high shear rates. More specifically, the compositions of the present invention preferably have Newtonian plateau viscosities of less than 5 mPa*sec at shear rates above 25 sec$^{-1}$, with viscosities in the range of 0.1 to 1 mPa*sec being most preferred.

The above-discussed modification of rheological properties provided by the inorganic nanoparticles may be utilized to enhance the retention time of the compositions of the present invention in the eye or ear, or improve the flow characteristics of the compositions.

The ophthalmic and otic compositions of the present invention may contain various ancillary substances, in addition to the above-described synthetic inorganic nanoparticles and pharmaceutically active agents, such as buffers and tonicity adjusting agents. The ophthalmic and otic compositions of the present invention will generally be formulated as sterile aqueous solutions, suspensions, dispersions or gels. The compositions must be formulated so as to be compatible with ophthalmic and otic tissues. The ophthalmic solutions, suspensions and dispersions of the present invention will generally have an osmolality of from about 200 to about 400 milliosmoles/kilogram water ("mOsm/kg"). All of the compositions of the invention will have a physiologically compatible pH.

The ophthalmic and otic compositions of the present invention that are packaged as multi-dose products may contain one or more ophthalmically acceptable biocides in an amount effective to prevent microbial contamination of the compositions by microbes, such as bacteria and fungi. The biocides utilized for this purpose are referred to herein as "antimicrobial preservatives".

The invention is not limited relative to the types of biocides that may be utilized as antimicrobial preservatives. The preferred biocides include: chlorhexidine, polyhexamethylene biguanide polymers ("PHMB"), polyquatemium-1, and the amino biguanides described in co-pending U.S. patent application Ser. No. 09/581,952 and corresponding International (PCT) Publication No. WO 99/32158, the entire contents of which are hereby incorporated in the present specification by reference. The use of surface-active biocides is preferred.

The preferred antimicrobial agents are polyquatemium-1 and amino biguanides of the type described in U.S. patent application Ser. No. 09/581,952 and corresponding International (PCT) Publication No. WO 99/32158. The most preferred amino biguanide is identified in U.S. patent application Ser. No. 09/581,952 and corresponding PCT publication as "Compound Number 1", and has the following structure:

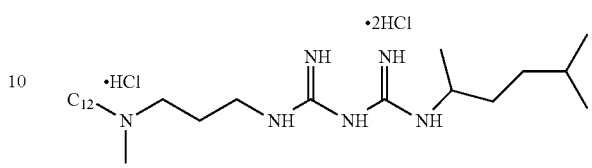

This compound is referred to below by means of the code number "AL8496".

The levels of antimicrobial activity required to preserve ophthalmic and otic pharmaceutical compositions from microbial contamination are well known to those skilled in the art, based both on personal experience and official, published standards, such as those set forth in the United States Pharmacopoeia ("USP") and similar publications in other countries. The amount of antimicrobial preservative required for this purpose is referred to herein as "an effective amount".

The compositions may also contain one or more components to enhance the antimicrobial activity of the compositions, such as: a borate/polyol complex (e.g., boric acid/propylene glycol), as described in U.S. Pat. No. 6,143,799 (Chowhan, et al.); a low molecular weight amino alcohol (e.g., AMP), as described in U.S. Pat. No. 6,319,464 B2 (Asgharian); or a low molecular weight amino acid (e.g., glycine), as described in U.S. Pat. No. 5,741,817 (Chowhan, et al.). The entire contents of the above-referenced patents are hereby incorporated in the present specification by reference. The above-cited components may be used either alone or in combination with conventional antimicrobial agents such as polyquatemium-1.

The compositions of the present invention are further illustrated by the representative formulations described in the following examples.

EXAMPLES

The table below provides examples of ophthalmic drug suspensions containing rimexolone. These compositions are useful in the treatment of ocular inflammation. All concentrations in the table are expressed as weight/volume percent.

| Ingredient | 9534-38A | 9534-38B | 9534-38C | 9534-38D | 9534-38E | 9534-38F | 9534-38G | 9534-38H | 9534-38I |
|---|---|---|---|---|---|---|---|---|---|
| Laponite ® XLG | 0.25 | 0.125 | 0.05 | 0.5 | 0.25 | 0.5 | 0.5 | 0.25 | 0.25 |
| Rimexolone | — | — | — | 0.1 | 0.1 | 0.1 | 0.1 | 0.1 | 0.1 |
| BAC | — | — | — | — | — | 0.01 | — | 0.01 | — |
| AL-8496A | — | — | — | — | — | — | 0.0004 | — | 0.0004 |
| Poloxamine 1304 | 0.1 | 0.1 | 0.1 | 0.1 | 0.1 | 0.1 | 0.1 | 0.1 | 0.1 |
| Tween 80 | 0.1 | 0.1 | 0.1 | 0.1 | 0.1 | 0.1 | 0.1 | 0.1 | 0.1 |
| EDTA | 0.1 | 0.1 | 0.1 | 0.1 | 0.1 | 0.1 | 0.1 | 0.1 | 0.1 |
| Sodium Chloride | 0.4 | 0.4 | 0.4 | 0.4 | 0.4 | 0.4 | 0.4 | 0.4 | 0.4 |
| Propylene Glycol | 1.0 | 1.0 | 1.0 | 1.0 | 1.0 | 1.0 | 1.0 | 1.0 | 1.0 |
| HPMC | 0.4 | 0.4 | 0.4 | 0.4 | 0.4 | 0.4 | 0.4 | 0.4 | 0.4 |
| Sodium Borate | 0.4 | 0.4 | 0.4 | 0.4 | 0.4 | 0.4 | 0.4 | 0.4 | 0.4 |
| Purified Water | QS | QS | QS | QS | QS | QS | QS | QS | QS |
| pH | 7.8 | 7.8 | 7.8 | 7.8 | 7.8 | 7.8 | 7.8 | 7.8 | 7.8 |
| *Viscosity mPa · s at 61.15 s$^{-1}$ | 7.89 ± 0.25[1] | 9.78 ± 0.32 | 10.09 ± 0.30 | 13.20 ± 0.01 | 12.36 ± 0.54 | TBD | TBD | TBD | TBD |

*Determined using Brookfield DVIII+ - ULA spindle-room temperature-not controlled

We claim:

1. An ophthalmic pharmaceutical composition comprising a therapeutically effective amount of an ophthalmic drug and an amount of smectite clay nanoparticles of from 0.1 to 1 w/v %, wherein the composition has a Newtonian plateau viscosity in the range of 0.1 to 1 mPa*sec at the shear rates above 25 $sec^{-1}$ and has a physiologically compatible pH and osmolality from about 200 to about 400 milliosmoles/kilogram water and the nanoparticles have particle dimensions less than 100 nm but greater than 1 nm.

2. A composition according to claim 1 wherein the nanoparticles have: (a) particle dimensions less than 100 nm, but greater than 1 nm, with a standard deviation of the distribution of less than 10%; (b) surface areas ranging from 30 to 1000 m2/g; and (c) an overall negative surface charge at a pH in the range of 6.0 to 7.8.

3. A composition according to claim 1, wherein the drugs are selected from anti-glaucoma agents, dopaminergic antagonists, anti-infectives, non-steroidal and steroidal anti-inflammatories, proteins, growth factors, mucosecretagogoues, angiostatic steroids, antihistamines, mast cell stabilizers and immunomodulators.

4. A composition according to claim 1, wherein the amount of nanoparticles is not greater than 0.5 w/v %.

5. A composition according to claim 1, wherein the pH is in the range of 6.0 to 7.8.

6. A composition according to claim 3, wherein the steroidal anti-inflamatory drug is rimexolone.

7. A composition according to claim 3, wherein the anti-infective drug is moxifloxacin.

8. A method of providing carriers for ophthalmic drugs, said method comprising adding synthetic smectite clay nanoparticles in an amount of from 0.1 to 1 w/v % to an ophthalmic pharmaceutical composition having said drugs, wherein the composition has a Newtonian plateau viscosity in the range of 0.1 to 1 mPa*sec at the shear rates above 25 $sec_{-1}$ and has a physiologically compatible pH and osmolality from about 200 to about 400 milliosmoles/kilogram water and the nanoparticles have particle dimensions less than 100 nm but greater than 1 nm.

9. A method according to claim 8, wherein the drugs are selected from anti-glaucoma agents, dopaminergic antagonists, anti-infectives, non-steroidal and steroidal anti-inflammatories, proteins, growth factors, mucosecretagogoues, angiostatic steroids, antihistamines, mast cell stabilizers and immunomodulators.

10. A method according to claim 8, wherein the amount of nanoparticles is not greater than 0.5% w/v %.

11. A method according to claim 8, wherein the pH is in the range of 6.0 to 7.8.

12. A method according to claim 9, wherein the steroidal anti-inflamatory drug is rimexolone.

13. A method according to claim 9, wherein the anti-infective drug is moxifloxacin.

14. A method of delivering a drug to the eye, which comprises utilizing smectite clay nanoparticles having dimensions less than 100 nm but greater than 1 nm in an amount of from 0.1 to 1 w/v % as carriers for the drug in a composition which has a Newtonian plateau viscosity in the range of 0.1 to 1 mPa*sec at shear rates above 25 $sec_{-1}$ and has a physiologically compatible pH and osmolality from about 200 to about 400 milliosmoles/kilogram water, applying said composition to the eye.

15. A method according to claim 14, wherein the drugs are selected from anti-glaucoma agents, dopaminergic antagonists, anti-infectives, non-steroidal and steroidal anti-inflammatories, proteins, growth factors, mucosecretagogoues, angiostatic steroids, antihistamines, mast cell stabilizers and immunomodulators.

16. A method according to claim 15, wherein the amount of nanoparticles is not greater than 0.5 w/v %.

17. A method according to claim 15, wherein the pH is in the range of 6.0 to 7.8.

18. A method according to claim 15, wherein the steroidal anti-inflamatory drug is rimexolone.

19. A method according to claim 15, wherein the anti-infective drug is moxiflacin.

* * * * *